United States Patent
Baker

(10) Patent No.: US 9,648,857 B2
(45) Date of Patent: May 16, 2017

(54) METHODS OF STUDYING TOLERANCE IN MHC-II TRANSGENIC ANIMALS

(75) Inventor: Matthew Baker, Cambridge (GB)

(73) Assignee: Antitope Limited, Cambridge (GB)

( * ) Notice: Subject to any disclaimer, the term of this patent is extended or adjusted under 35 U.S.C. 154(b) by 673 days.

(21) Appl. No.: 11/719,876

(22) PCT Filed: Nov. 23, 2005

(86) PCT No.: PCT/GB2005/004498
§ 371 (c)(1),
(2), (4) Date: May 22, 2007

(87) PCT Pub. No.: WO2006/056769
PCT Pub. Date: Jun. 1, 2006

(65) Prior Publication Data
US 2009/0226893 A1 Sep. 10, 2009

(30) Foreign Application Priority Data
Nov. 23, 2004 (GB) .................................. 0425713.5

(51) Int. Cl.
*A01K 67/027* (2006.01)
*A01K 67/02* (2006.01)
*A61K 39/00* (2006.01)

(52) U.S. Cl.
CPC ...... *A01K 67/0278* (2013.01); *A01K 67/0276* (2013.01); *A01K 2227/105* (2013.01); *A01K 2267/03* (2013.01); *A61K 39/00* (2013.01)

(58) Field of Classification Search
CPC ............ A01K 2217/05; A01K 2207/15; A01K 2227/105; A01K 2267/03; A01K 67/0275; A61K 39/00; A61K 2039/505
USPC ................................................ 800/18, 3, 22
See application file for complete search history.

(56) References Cited

U.S. PATENT DOCUMENTS 5,821,337 A 10/1998 Carter et al.
6,277,969 B1 8/2001 Le et al.

FOREIGN PATENT DOCUMENTS

WO 9004036 A1 4/1990
WO 03042247 A2 5/2003

OTHER PUBLICATIONS

Schellekens (2002) Nat. Rev., vol. 1, 457-462.*
Hall et al. (1999) Rheumatology, vol. 38, 697-704.*
Kellerman et al. "Developing the Xenomouse Technology for Evaluating Immunogenicity" . (Mar. 2004) AntiBoz2—An International Forum: Predicting the Next Wave of Protein-based Therapies and Immunodiagnostics, meeting abstract.*
Ichino et al. (1999) J. Immunol., vol. 162, 3814-3818.*
Ilan et al. (1996) J. Clin. Invest., vol. 98, 2640-2657.*
Hudzuak et al, "Monoclonal Antibody has antiproliferative effects in vitro and sensitizes human breast tumor cells to tumor necrosis factor". Molecular and Cellular Biology, pp. 1165-1172, Mar. 1989.
Orlandi et al., "Cloning immunoglobulin variable domains for expression by the polymerase chain reaction." Proc. Natl. Acad. Sci. USA vol. 86, pp. 3833-3837, May 1989.
Carter et al, "Humanization of an anti-p185 her 2 antibody for human cancer therapy." Proc. Natl. Acad. Sci. USA vol. 89, p. 4285, Jan. 1992.
Altmann, D.M. et al., "The T Cell response of HLA-DR transgenic mice to human myelin basic protein and other antigens in the presence and absence of human CD4." J. Exp. Med. vol. 181, Mar. 1995.
Nicolson et al., "Antibody repertories of four- and five- feature translocus mice carrying human immunoglobulin heavy chain and k and h light chain yeast artificial chromosomes." J. Immunol. vol. 163, Sep. 1999.
Madsen L. et al., "Mice lacking all conventional MHC class II genes." Proc. Natl. Acad. Sci. USA, vol. 96, 1999, pp. 10338-10343.
Loirat, D. et al., "Multiepitopic HLA-A*0201-restricted immune response against hepatitis B surface antigen after DNA-based immunization." J. Immunol vol. 165, 2000, pp. 4748-4755.
Vandenbark A.A. et al., "Recombinant TCR ligand tolerance to myelin oligodendrocyte glycoprotein 35-55 peptide and reverses clinical and histological signs of chronic experimental autoimmune encephalomyelitis in HLA-DR2 tansgenic mice." The Journal of Immunology vol. 171, 2003, pp. 127-133.
Patel et al., Identification of immunodominant T cell epitopes of human glutamic acid decarboxylase 65 by using HLA-DR (alpha1*0101, beta1*0401) transgenic mice, PNAS USA 1997 94:8082-8087.

* cited by examiner

*Primary Examiner* — Anne Marie S Wehbe
(74) *Attorney, Agent, or Firm* — Stradley Ronon Stevens & Young LLC

(57) ABSTRACT

Novel methods of testing the immunogenicity of variant antigens are provided. In particular, methods based on the use of transgenic animals are provided, wherein the transgenic animal is tolerized to a particular antigen and is then exposed to variants of the antigen and immune responses are determined. In one embodiment the transgenic animal is a mouse which is transgenic for human MHC class II molecules and the immunogenicity of libraries of variant antibodies are tested.

10 Claims, No Drawings

METHODS OF STUDYING TOLERANCE IN MHC-II TRANSGENIC ANIMALS

The present invention relates to in viva systems for testing the immunogenicity of protein variants. In particular, the invention relates to methods using mice transgenic for human MHC class II molecules where such mice are made tolerant to a specific protein and then tested with variants of the specific protein for induction of immunogenicity. In addition, the present invention relates to in vivo systems for selecting proteins from a library of protein variants for reduced immunogenicity whereby tolerised human MHC transgenic mice are injected with libraries of cell lines or particles associated with different variant proteins whereby specific cell lines or particles associated with variant proteins with lower immunogenicity than other proteins in the library are selected in vivo.

Current methods for testing candidate pharmaceutical proteins for potential immunogenicity in humans are limited primarily because non-human species have different MHC (major histocompatibility antigen) molecules from humans and thus immune responses to injected proteins in test animals do not reflect prospective immune responses to the same proteins in humans. Therefore it is important to test proteins for immunogenicity using either human cells or cells with human MHC. A particularly valuable approach is to test proteins in T cell proliferation assays using human blood samples. However, this approach measures T cell responses to the test protein in vitro and, as yet, no in vitro immunogenicity methods resulting in the production of antibodies as occurs in vivo have been demonstrated. Alternative approaches could use mice either reconstituted with human T and B cells or transgenic mice where the resident mouse MHC and, in some cases, the T cell receptor molecules have been replaced by their human counterparts. These approaches, however, may not result in accurate prediction of immunogenicity in humans because they do not take account of tolerance, especially tolerance in the human immune system to normal human proteins. For example, a mouse transgenic for human MHC would still be expected to mount an immune response against an injected human protein because the mouse would not be tolerant to such a human protein. There is thus a need for improved methods to facilitate in vivo immunogenicity testing of proteins and protein variants which take account of normal tolerance to proteins in the species.

Thus, in a first aspect the present invention provides method for testing the immunogenicity of a variant antigen, derived from a mammalian antigen, in a non-human mammal transgenic for said mammalian MHC class II molecules, wherein the non-human mammal is not the source of the mammalian antigen, the method comprising:

(a) rendering said transgenic mammal tolerant to the mammalian antigen through contact with the mammalian antigen;
(b) contacting said transgenic mammal with said variant antigen; and
(c) measuring the immunogenicity of said variant antigen in said transgenic mammal.

The present invention provides novel in vivo systems for testing e.g., the immunogenicity of proteins and protein variants. As discussed herein, the variant antigen is derived from a mammalian antigen. Variant antigens can include protein or polypeptide sequences which have additions, deletions or substitutions or which have been derivatised by chemical means. The antigen is not from the non-human transgenic mammal used in the method.

In particular, the invention relates to methods using mice transgenic for human MHC class II molecules allowing presentation of human T cell epitopes and testing of potential immunogenicity to human proteins and protein variants in a mouse background.

In one embodiment of the present invention, tolerance to a human protein is induced in neonatal mice expressing germline human MHC class II (HLA-tg) genes by injecting low concentrations (for example, equivalent to physiological amounts found in human serum and/or other tissue) of protein. Proteins are preferably monomeric and administered intravenously in an immunologically 'inert' buffer such as saline or phosphate-buffered saline (PBS). In such systems, the frequency of dose to induce tolerance will vary depending on the protein to which tolerance is induced. For example, proteins normally present at high serum concentrations most likely need to be administered more frequently to induce tolerance than those normally found at low physiological concentrations.

Preferably, immature mice (for example neonatal mice) will be used in order to ensure that the tolerising protein is present during T cell development and therefore induces central tolerance.

Typically, mice up to age 6 weeks will be given repeat administrations where production of mature CD4+ and CD8+ T cells from the thymus decreases (normally adulthood). Having established tolerance to the test protein or invariant forms of the test variant proteins, the tolerised mice will then be injected with the test protein or protein variants and subsequently tested for immunogenicity against the test protein or protein variants. In mice with intact immunoglobulin genes, immunogenicity may be measured by production of antibodies against the test protein or protein variants. Alternatively, other assays related to immunogenicity may be undertaken such as assays to measure test protein-specific T or B cell responses using peripheral blood, spleen or Peyer's Patch from tolerised HLA-tg mice.

In another embodiment of the present invention, tolerance is induced in mice by backcrossing human HLA-tg mice onto mice expressing a human transgene for the protein of interest. For example, human HLA-tg mice that express human IgG can be produced that are tolerant for human IgG. Where human IgG is not expressed in such a way as to allow variable (V) region somatic mutation, translocation or rearrangements, or change in constant (C) region by class switching, then these mice will be tolerant to the specific human IgG sequences expressed but intolerant to certain human V region somatic mutation, translocation or rearrangements or change in C region by class switching. Where human IgG is expressed in such a way as to allow V region somatic mutation, translocation or rearrangements or C region class switching, then these mice will be not only tolerant to a specific human IgG containing a specific germline V and C region sequence but also to human IgG that has undergone affinity maturation and is specific for any antigen.

Under these conditions it is possible to produce a transgenic mouse expressing endogenous human MHC class II and a human protein to which central tolerance in the context of human MHC class II can be achieved. The number of copies of the human transgene (encoding the human protein of interest) incorporated into the mouse genome or the efficiency of expression of the transgene (determined by different factors such as efficiency of transcription and translation, and the localisation of transgenes within the mouse genome) will determine the amount of protein expressed and may be varied to generate mice with different expression levels for the human transgene so that only mice expressing 'physiological amounts' of the transgene are selected for backcrossing onto HLA-tg mice.

Using either the injection or transgene approaches to induce tolerance to human proteins in HLA-tg mice, it will be preferable to use mice expressing a single human MHC class II allele. Thus the processes described above are employed to induce tolerance in a panel of mice each expressing a single MHC class II allotype. Multiple HLA-tg mice will be selected such that collective coverage of as large a proportion as required of human MHC class II allotypes is achieved. It will be understood that, within the scope of the invention, other methods may be employed to render HLA-tg mice tolerant to the specific protein or protein variant of interest including methods of inducing specific leucocytes tolerant to the specific protein, methods for deleting specific leucocytes reactive to the specific protein and methods for modulating the immune system during exposure to the specific protein or variants such that tolerance is induced. It will also be understood that, where possible, mice which do not express mouse homologues of the specific test protein or protein variants will be preferred for use in the present invention to avoid any inherent tolerance of these mice to the test protein or protein variants.

It will be understood that tolerised HLA-tg mice from the above embodiments of the invention can be used in a variety of ways for testing immunogenicity of specific proteins or protein variants or for ranking a set of protein variants for immunogenicity. In mice tolerised to a specific protein, immunogenicity can be tested to variants of that protein including variants with amino acid changes within the protein, variants with differences in amino acid modifications such as deamidation or glycosylation, formulation differences, physical differences (e.g. differences in aggregation) or any other differences which might result in immunogenicity. In particular, the consequences of high and prolonged dosing can be determined by administration of the protein of interest at increasing concentrations to tolerised nice. Immunogenicity related to route of administration can also be investigated where proteins can be administered at different locations in tolerised mice and resultant immunogenicity assessed. It will be understood that analysis of immunogenicity in tolerised mice can be undertaken by a variety of methods including testing blood samples or other tissue samples (such as Peyer's Patch, spleen) from mice after injection of the test protein or protein variants for antibodies (such as by ELISA, RIPA, FACS and surface plasmon resonance), testing for T cell proliferation or activation, testing for production of protein-reactive T cells, for example by binding of specific peptide-MHC complexes, testing of T or B cells by measuring cytokine production, proliferation, cell surface marker expression, $Ca^{2+}$ flux, PCR or DNA fingerprinting, testing for the emergence of specific immune reactive B or T cells, or by any other means of testing immunogenicity. It will be understood that analysis of immunogenicity in tolerised mice with intact functional immunoglobulin genes can be undertaken by injection of a single test protein and measurement of immunogenicity via production of antibodies, for example by measuring the formation of antibodies which bind to the injected test protein, or alternatively by injection of a mixture of test proteins or protein variants, for example by testing antibodies formed in response to the injected mixture for binding to specific proteins or protein variants within the mixture (for example by immunoblotting onto an array of individual test proteins or protein variants; or by isolating antibodies or antibody sequences from the injected mice and determining the specificity of binding of these antibodies for binding to individual test proteins or protein variants).

The invention will be particularly suited for immunogenicity testing of different human (or humanised) monoclonal antibodies or fragments thereof whereby HLA-tg mice are tolerised to human monoclonal antibody sequences and whereby such mice can then react to variable region mutations associated with human antibodies with somatic mutations (or other non-germ-line mutations, translocations or rearrangements) in the variable regions. In these cases, mice with deleted or non-expressing endogenous mouse immunoglobulin genes will be preferred. As such, the invention will be particularly suitable for comparative immunogenicity testing of panels or libraries of human or humanised monoclonal antibodies in order to identify those antibodies with no or with low level immunogenicity. In particular, the facility of the invention to test mixtures of different human (or humanised) monoclonal antibodies or fragments thereof injected into the same mouse and to determine, for example by immunoblotting, the immunogenicity of individual antibodies within the mixture, is especially suited to rapid analysis of large libraries of antibodies. For antibodies displayed on particles, such as bacteriophage, cells or other particles, the invention encompasses direct injection of antibody libraries upon the display particle preferably (but not essentially) where the mouse is tolerant to the injected particle.

As an extension to the present invention, it will be understood that HLA-tg mice additionally transgenic for the protein or protein variants of interest can be used for generation of protein variants with tolerance generated relative to the specific HLA background e.g. human HLA. For example, human monoclonal antibodies can be developed following injection of an antigen on a background of human HLA when the germline human IgG is expressed in such a way as to allow subsequent V region somatic mutation, translocation or rearrangements or C region class switching. Mice will then be tolerant, in the context of the human HLA expressed in these mice, to human IgG that has undergone affinity maturation and is specific for any antigen. This then may reduce the prospect that human antibodies generated within such human HLA-tg mice will be non-immunogenic in humans.

It will be understood that HLA-tg mice tolerant or transgenic for the protein or protein variants of interest can be used in a variety of immunogenicity screening applications relating to the generation and testing of pharmaceuticals for man. For example, in addition to measuring the immunogenicity of protein variants, such HLA-tg mice can be used to map immunogenic regions or immunogenic sequences within proteins or protein variants of interest. In particular, peptides spanning part or all of the sequence of the protein or protein variants of interest can be tested by direct injection into HLA-tg mice and subsequent measurement of immunogenicity such as by measurement of T cell proliferation from serum or tissue isolates. In this way, such HLA-tg mice will be particularly useful for mapping T cell epitopes in the sequences of proteins or protein variants. Such T cell epitopes sequences can then be modified within the protein or protein variants in order to eliminate the epitopes prior to use of the protein or protein variants as potential pharmaceuticals for man.

It will be understood that HLA-tg mice tolerant or transgenic for the protein or protein variants of interest can be used in a variety of ways to test the immunogenicity of proteins or protein variants of interest following injection at various doses, in various formulations, at various timepoints and for repeat dosages, from various preparation batches including manufacturing batches and in the presence of various agents whether co-injected or present within the HLA-tg mice such as infectious disease agents, various other cells, other pharmaceuticals, chemical/environmental agents and in HLA-tg mice which are immunocompromised or subjected to various insults, injuries or illnesses.

In a further extension to the present invention, HLA-tg mice tolerised to the protein of interest are used to directly select, from a library of variant proteins, those proteins with low immunogenicity compared to other members of the library. In such a selection, the immunogenic response of the HLA-tg mouse to a specific protein or protein variant directly leads to selection against that protein or protein variant such that other proteins with low immunogenicity are enriched or identified. For example, antibodies induced by an immunogenic protein or protein variant directly bind to the immunogenic protein or protein variant as the basis for selection against this variant. Several methods can be used to achieve such selection. For example, serum immunoglobulin from HLA-tg mice injected with a library of variant proteins could be used to preabsorb (e.g. by immunoprecipitation or immunochromatography) immunogenic protein variants from the library leaving less immunogenic or non-immunogenic variants which could be identified either at the protein molecular level (e.g. by mass spectrometry-based sequencing or fingerprinting) or by virtue of a particle associated with the variant e.g. a peptide sequence tag, a nucleic acid sequence or any other molecular code used to identify the specific protein variant in the library. Other in vitro methods could be used to identify variants with low immunogenicity such as methods where such variants are captured onto a solid phase only where no mouse antibody is present to interfere with the specific capture site on the protein variant. For example, in the case of a library of human IgGs, a solid phase antigen preparation could be used to capture antibodies where no mouse immunoglobulin has bound to the antigen-binding site on the human IgG.

As an alternative to in vitro methods for selection of protein variants from a library with low immunogenicity, in vivo selection methods can be used where the less immunogenic or non-immunogenic variants are selected in vivo. Selection in vivo is by virtue of antibodies induced in the tolerised HLA-tg mouse either binding to and clearing specific variants from the circulation or injected compartment within the mouse or by directly killing or engulfing live cells expressing such variants or particles bound to such variants, for example live myeloma cells by virtue of surface IgG or live bacteriophage by ADCC (antibody-dependant cytotoxicity) or CDC (complement-dependant cytotoxicity), or inert particles linked to specific variants by antibody-dependant pinocytosis. In a basic method, the HLA-tg mouse is injected with the library of protein variants (for example, intravenously) and, at a selected timepoint, an analysis is made of which protein variants still remain uncleared by host immunoglobulin. This analysis can be performed, for example, by purifying members of the library of protein variants at the selected timepoint and identifying variants enriched in the library following in vivo selection. Alternatively, where protein variants are associated with nucleic acids (for example, within a live cell such as a myeloma or bacteriophage), the analysis can be made by direct amplification and DNA sequencing of genes associated with the enriched protein variants or DNA fingerprinting before and after selection to identify bands in the fingerprint enriched by the selection, such bands then providing for subsequent identification of the enriched protein variant. In cases where protein variants are selected on live cells or particles and where such cells or particles themselves induce immunogenicity, HLA-tg mice can be tolerised to such cells or particles, for example by injection or further addition to the transgenic background, or other means used to avoid interference of such cells and particles in the selection process for protein variants.

An example of the invention is the in vivo selection of antibody variants produced by live cells whereby a population of live cells such as mouse myeloma (e.g. hybridoma) cell library expressing human IgGs or bacteriophage cells displaying antibody V regions are injected into tolerised HLA-tg mice. These mice will produce antibodies to any immunogenic human IgGs produced by the injected myeloma cells or bacteriophage and these antibodies will bind to surface IgG, thus inhibiting the growth of cells/infectivity of phage or leading to destruction (via ADCC, CDC or endocytosis) of these cells or phage. In such a manner, tolerised HLA-tg mice will select against myeloma cells or bacteriophage producing immunogenic antibodies and cells/phage producing antibodies with low or no immunogenicity will be enriched from the injected population. Such cells/phage producing desirable antibodies with low or no immunogenicity can then be recovered, for example by retrieving and culturing enriched myeloma cells, by use of cell sorting using anti-Ig staining to sort antibody-producing cells, or by amplifying selected phage by cycled infection of bacteria. Alternatively, for non-immortalised mammalian cells such as B cells, standard immortalisation and cloning procedures may be used such as involving EBV transformation or cell fusion or other means to immortalise prior to cloning, or nucleic acid amplification methods such as PCR may be used to isolate V region genes from the selected antibodies. In addition, comparative analysis of B cell populations before and after selection in tolerised HLA-tg mice can be used to identify enriched B cell lineages or enrichment of specific antibodies, for example by comparative PCR, comparative DNA fingerprinting or comparative mass spectrometry methods such as LC-MS.

It will be understood by those skilled in the art that there are many variations of the methods of the present invention for testing the immunogenicity of proteins and protein variants but that these should be considered within the scope of the present invention which uses HLA-tg mice tolerised to a specific protein or protein variants as a background to measure the immunogenicity of proteins or to select proteins with low or absent immunogenicity or to compare and rank different proteins based on immunogenicity. It will be understood that HLA-tg mice tolerised to specific proteins are novel especially transgenic mice with one or more human protein transgenes additional to the human HLA transgene. In particular, human HLA-tg mice with additional human IgG transgenes, preferably encoding as much of the human heavy and light chain variable region immunoglobulin loci as possible, are novel and particularly useful in the immunogenicity testing of therapeutic monoclonal antibodies or in the in vivo selection of therapeutic antibodies from a selection of variants. It will also be understood that the present invention applies particularly to the generation of proteins for use as pharmaceutical or in vivo diagnostic agents for humans whereby human HLA-tg mice would be used and proteins with little or no immunogenicity would be selected using the same HLA background as would be present in humans and using similar levels of tolerance (if any) that would be expected in humans. It will be appreciated that, within the present invention, organisms other than mouse could be used where human HLA molecules can either be provided via transgenics or by other means such as injection of human antigen-presenting cells. It will also be appreciated that for purposes other than in human pharmaceuticals (e.g. for animal pharmaceuticals), HLA backgrounds other than human could also be used with tolerance induced to proteins of the species used. It will be appreciated that tolerised HLA-tg animals could also be used within the scope of the present invention and using some of the methods to select for proteins or protein variants with high immunogenicity for use in vaccination.

It will also be understood by those skilled in the art that there are many variations of the methods of the present invention for selecting proteins or protein variants for low immunogenicity via a wide range of in vitro or in vivo testing or isolation methods but that these should be considered within the scope of the present invention which uses HLA-tg mice tolerised to the specific protein or protein variants as a background for such selection. It will also be understood that analysis or selection of proteins or protein variants by tolerised HLA-tg mice will usually require parallel analysis or selection in a range of background HLA allotypes usually via a panel of transgenic mice with different allotypic HLA genotypes. For the selection of proteins or protein variants for use in humans, a range of MHC allotypes represented in at least 50% of the human population is desirable in order to avoid selecting proteins on too few allotypes which may lead to immunogenicity once the protein is injected into humans with other allotypes not present in the mice used for analysis or selection.

It will also be understood by those skilled in the art that the present invention should not be restricted to use of transgenic mice but could also include other animals rendered transgenic for human MHC class II and used in the same way to measure the immunogenicity of protein variants or to select for protein variants with low immunogenicity. It will also be understood that the present invention should not be limited to proteins and could apply to the measurement of the immunogenicity of non-protein variants or to select for non-protein variants with low immunogenicity such as organic chemicals, inorganic chemicals, allergens, cosmetics, environmental pollutants, infectious agents and foodstuffs. It will also be understood that the present invention could be used for development and testing of vaccines for human use, for example in determining effective T cell epitopes for use in human vaccines, in screening for effective subunit or DNA vaccines, in testing different vaccine formulations and routes of administration for prospective effectiveness in humans, and in testing potential vaccines for prevention of or induction of immune responses against disease agents such as infectious disease, cancer and inflammation whereby such diseases are introduced or induced in the mice (or other animals) prior to testing for potential vaccines. It will also be understood that HLA-tg transgenic animals of the present invention could, in addition to human MHC class II, be transgenic for individual components or combinations thereof of other human molecules of the immune system such as T cell receptor, MHC class I, CD4, CD8 and other cytokines or receptors, in each case to introduce additional components of the human immune system towards mimicking a range of different molecular events in relation to human immunity. In the same manner, animals of the present invention could be transplanted with one or more cells of the human immune system to facilitate a human immune response to a test protein or non-protein.

The following examples are provided to illustrate the present invention and should not be considered as limiting in scope from the invention;

EXAMPLE 1

Generation of Immunogenic/Non-Immunogenic Tests Antibodies

The immunogenic test antibody chosen for the study was the chimeric anti-TNFα antibody known as Remicade® (Le et al., U.S. Pat. No. 6,277,969) with variable regions derived from the mouse cA2 antibody (hereinafter "Remicade"). A further test antibody used was a humanised anti-HER2 antibody known as Herceptin® (Carter et al., Proc. Nat. Acad. Sci. USA, vol 89 (1992) p4285, U.S. Pat. No. 5,821, 337) (hereinafter Herceptin). The non-immunogenic control antibody used was a derivative of Herceptin (hereinafter "GLH"=germline Herceptin®) incorporating human germline Vh3-53 and Vκ O12 sequences.

Recombinant DNA and antibody techniques were performed using methods well known in the art and, as appropriate, supplier instructions for use of enzymes and antibodies used in these methods. Sources of general methods included Molecular Cloning, A Laboratory Manual, $3^{rd}$ edition, vols 1-3, eds. Sambrook and Russel (2001) Cold Spring Harbor Laboratory Press; Current Protocols in Molecular Biology, ed. Ausubel, John Wiley and Sons; and, Antibodies, A Laboratory Manual, eds. Harlow and Lane (1988), Cold Spring Harbor. Sequences corresponding to Remicade®, Herceptin® and GLH antibody V regions were created using, for each chain, eight synthetic oligonucleotides of 30-60 amino acids in length encoding the entire human VH and VL sequences. Separate VH and VL oligonucleotides were first phosphorylated, mixed at equal molar ratios, heated to 94° C. for 5 min in a thermal cycler followed by cooling to 65° C. and incubation at 65° C. for 2 min. Incubations were then continued at 45° C. for 2 min., 35° C. for 2 min., 25° C. for 2 min and 4° C. for 30 min. Oligonucleotides were then ligated using T4 DNA ligase (Life Technologies, Paisley, UK) at 14° C. for 18 hours.

To each of the VH and VL oligonucleotide mixtures, additional oligonucleotides encoding a 5' flanking sequence, including a Kozak sequence, the leader signal peptide sequence and the leader intron, and 3' flanking sequence, including the splice site and intron sequence, were added and annealed as above. The VH and VL expression cassettes produced were cloned as HindIII to BamHI fragments into the plasmid vector pUC19 and the entire DNA sequence was confirmed. These were transferred to the expression vectors pSVgpt and pSVhyg (Orlandi et al., Proc. Natl. Acad. Sci. USA, 86 (1989) 3833-3837) which include human IgG1 or human κ constant regions respectively and markers for selection in mammalian cells.

The host cell line for antibody expression was NSO, a non-immunoglobulin producing mouse myeloma, obtained from the European Collection of Animal Cell Cultures, Porton, UK (ECACC No 85110503). The heavy and light chain expression vectors were co-transfected into NSO cells by electroporation. Colonies expressing the gpt gene were selected in Dulbecco's Modified Eagle's Medium (DME supplemented with 10% foetal bovine serum, 0.8 µg/ml mycophenolic acid and 250 µg/ml xanthine. Transfected cell clones were screened for production of human antibody by ELISA for human IgG. Antibodies were purified using Prosep®-A (Millipore, Watford, UK) and concentration was determined by ELISA for human IgGκ (Pharmacia Biotech, St Albans, UK). Purified Remicade, Herceptin and GLH antibodies were tested for binding in two assays, one using immobilised human TNFα in a standard ELISA (described in WO 03/042247A2) and another using inhibition of proliferation of the HER2+ human breast tumour cell line SK-BR-3 as described by 4D5 (Hudziak et al., Mol. Cell. Biol., (March 1989) p1165-1172). The Remicade antibody demonstrated the expected binding to human TNFα in the ELISA assay but with no inhibition of SK-BR-3 cells. Herceptin did not bind to human TNFα whilst exhibiting inhibition of proliferation of SK-BR-3 cells. The GLH antibody showed neither binding to human TNFα nor inhibition of SK-BR-3 cells.

EXAMPLE 2

Human HLA Transgenic Mice Lacking Mouse Immunoglobulin Expression

Human HLA-DR1 transgenic mice lacking mouse MHC class II (Altmann, D. M. et al., J Exp Med 181 (1995) 867-875) were obtained from Imperial College, London UK. These were crossed with rice lacking immunoglobulin heavy chain (CΔ-/-) obtained from Babraham Institute, Cambridge UK (Bruggeman, EP0438474B1) and mice with the desired genotype of human HLA-DR1+/+, mouse MHC class II-/- and mouse Ig CΔ-/- were selected (hereinafter "hu DR+/IgCΔ-/-" mice). These hu DR+/IgCΔ-/- mice were then further crossed with mice lacking immunoglobulin light chains (λ/κ-/-, Babraham Institute) and mice with the desired genotype of human HLA-DR1+/+, mouse MHC class II-/-, mouse Ig CΔ-/- and mouse λ/κ-/- were selected (hereinafter "hu DR+/IgCΔ-/-λκ-" mice).

EXAMPLE 3

Induction of Neonatal Tolerance

Remicade, Herceptin and GLH antibodies were dialysed and diluted to 500 µg/ml in PBS and centrifuged at 20,000 g for 15 minutes at 4° C. A tolerising dose of 50 µl of individual antibodies was injected intraperitoneally into neonatal hu DR+/IgCΔ-/- mice within 30 hours birth (=day 0). Control mice were injected with 50 µl PBS. 50 µg doses of either Remicade, Herceptin and GLH antibodies together with 5 µg KLH control in total 200 MPL+TDM emulsion (RAS-Ribi adjuvant, product code R-700, Corixa Corp, Hamilton, Mont., USA) were then injected subcutaneously at days 10, 16 and 24. On day 32, mice were sacrificed for T cell proliferation assays. Red-blood cell-depleted, Ficoll-purified splenocytes were prepared and cultured at $5 \times 10^6$ cells in T25 flasks with antibody or KLH-pulsed gamma-irradiated LPS-blasts as described by Loirat, D., et al., J Immunol., 165 (2000) 4748-4755. After 7 days of culture, cells were plated at $5 \times 10^5$ cells per well in flat bottomed 96 well microplates with antibody or KLH-pulsed irradiated LPS-blasts and incubated for a further 72 hrs in complete RPMI+3% FCS. Cells were pulsed for the final 16 hrs with 1 µCi per well of $^3$H-thymidine and harvested onto filter-mates with a TOMTEC collector (PE Applied Biosystems, Warrington, UK). Radioactivity was measured on a micro-beat counter (PE Applied Biosystems) and results expressed as a stimulation index (SI) of cpm for antibody or KLH treatments vs PBS controls.

These results showed no significant SI>2 for animals tolerised with Remicade, Herceptin and GLH antibodies and then challenged with the same respective antibody in adjuvant. However, T cell responses (SI>2) were observed in 5 out of 10 mice in animals tolerised for purified polyclonal human IgG (huIgG) and then challenged with Remicade antibody. In contrast responses (SI>2) were detected in only 1 out of 10 huIgG tolerant mice after challenge with GLH, whilst for animals tolerised with Herceptin, no response (SI>2) was detected after challenge with GLH. Herceptin induced responses in 3 or 1 out of 10 mice tolerant to huIgG or GLH, respectively. All mice responded strongly to KLH in adjuvant resulting in strong KLH-specific responses in 90% of mice. These results demonstrated successful induction of neonatal tolerance in hu DR+/IgCΔ-/- mice to individual Remicade, Herceptin and GLH antibodies such that challenge with the same antibodies failed to induce T cell proliferation responses.

These results demonstrate the induction of significant T cell responses to the immunogenic Remicade antibody in mice tolerant to huIgG. Herceptin appeared to be less immunogenic (30% response rate) than Remicade (50% response rate) whereas GLH failed to induce responses in huIgG or Herceptin tolerant mice. This example illustrates a major part of the invention in the use of mice transgenic for human HLA-DR and rendered tolerant to specific immunoglobulins which parallels tolerance of humans to human immunoglobulins. Such transgenic mice can then be used to test various monoclonal antibodies for the induction of immunogenicity in transgenic human HLA-DR mice tolerised for specific immunoglobulins mice as a substitute for testing such antibodies in humans. The example shows that the Remicade antibody, which is significantly immunogenic in humans, induces significant immunogenicity in such transgenic tolerised human HLA-DR mice. In additional follow-on experiments, a human globulin preparation was used to tolerise hu DR+/IgCΔ-/- mice as in example 3 and these mice were then challenged with Remicade, Herceptin and GLH antibodies. The results showed that, as with tolerance to individual antibodies, Remicade injection resulted in SI>2 in >30% of mice whilst Herceptin and GLH showed no SI>2 in any animal.

EXAMPLE 4

Production of Human Ig Transgenic Mice

Mice transgenic for human IgM/κ (four-feature mice, Nicolson et al., J Immunol., 163 (1999) 6898-6906) were crossed with hu DR+/IgCΔ-/-λκ- mice (example 2) and and mice with the desired genotype of human IgM/κ, human HLA-DR1+/+, mouse MHC class II-/-, mouse Ig CΔ-/- and mouse λ/κ-/- were selected (hereinafter "hu IgCΔ-/-/κ" mice).

EXAMPLE 5

Testing of Immunogenicity in Human Ig Transgenic Mice

A control antibody for immunogenicity testing in hu IgM/κ mice was generated using a germline human VH1-2 and Vκ4.1 genes in conjunction with D1.7/J4 for VH and Jκ4 for Vκ (hereinafter "VH1-2/Vκ4.1" antibody). A recombinant human IgG1/κ antibody was generated as in example 1 and this antibody and the Remicade antibody from example 1 were both subjected to pepsin digestion to generate a dimeric $Fab_2$ fragment for injection. Prior to digestion, antibodies were dialysed in 0.2M sodium acetate buffer pH 4.0 and then adjusted to 2 mg/ml. 20 µg/ml pepsin (Sigma, Poole, Dorset UK) was added in an equal volume of 0.2M sodium acetate buffer pH 4.0 and incubated for 6 hrs at 37° C. 2M Trizma® base (Sigma) was added to adjust to pH7 and digestions were checked by gel electrophoresis. Antibody digests were dialysed overnight in PBS and then applied to two sequential Sephadex 75 columns (Pharmacia) to isolate $Fab_2$ fragments.

Hu IgM/κ mice were immunised with either 50 μg VH1-2/Vκ4.1 or Remicade $Fab_2$ fragments in CFA and were boosted at 4, 8 and 12 weeks each with 50 μg of the $Fab_2$ fragments in IFA. Production of human IgM/κ antibodies were tested by coating PVC microtitre plates overnight at 37° C. with either 5 μg/ml VH1-2/Vκ4.1, Remicade $Fab_2$ fragments or a control of whole GLH antibody (example 1) in PBS. Serum samples diluted in PBS, 5% chicken serum and 0.5% Tween-20 were then incubated in the wells for 1 hr at room temperature and, after washing, anti-human IgM Fc-HRP (Pharmacia) was added in the same buffer for 1 hr followed by addition of ABTS (Sigma) for 30 minutes and measurement of OD415 nm. This experiment demonstrated the induction of strong titres of IgM antibodies specific for Remicade $Fab_2$ fragment in animals immunised with Remicade $Fab_2$ but no induction of antibodies against VH1-2/Vκ4.1 in mice immunised with VH1-2/Vκ4.1 $Fab_2$ thus demonstrating the immunogenicity of Remicade in rice with a human immunoglobulin/human HLA-DR background. This example illustrates a major part of the invention in the use of mice transgenic for human HLA-DR and human immunoglobulin genes such that these mice are tolerant to a range of human immunoglobulin variable region sequences which parallels tolerance of humans to a range of human immunoglobulin variable region sequences. Such transgenic mice can then be used to test various monoclonal antibodies for the induction of immunogenicity as a substitute for testing such antibodies in humans. The example shows that the Remicade antibody induces significant immunogenicity in such transgenic human HLA-DR/Ig+ mice which parallels the finding in humans that immunogenicity to Remicade® is induced in a significant proportion of immunocompetent patients.

EXAMPLE 6

Selection of Antibodies in Human Ig Transgenic Mice 100 mg samples of VH1-2/Vκ4.1 and Remicade $Fab_2$ fragments in PBS (from example 5) were either co-injected or injected individually intravenously into hu IgM/κ mice. Repeated administration was performed after 10 days and 20 days after the initial dose. 2 hours after the final dose, mouse serum was analysed for the presence or absence of VH1-2/Vκ4.1 or Remicade $Fab_2$ fragments. Harvested serum was centrifuged at 20,000 g for 15 minutes at 4° C. and then dialysed overnight in PBS. $Fab_2$ fragments were then purified using Sephadex 75 as described in example 5 and tested as a dilution series for binding to human TNFα as in example 1 using anti-human Fab-HRP (Pharmacia). The results showed that for mice co-injected with VH1-2/Vκ4.1 and Remicade $Fab_2$ fragments, the recovered $Fab_2$ was >95% composed of VH1-2/Vκ4.1 in all mice tested. These results indicate that the more immunogenic Remicade $Fab_2$ had been cleared from the blood system compared to the less immunogenic VH1-2/Vκ4.1. It is possible that this effect is due to the formation of immune complexes with Remicade $Fab_2$ that facilitate a more rapid clearance than VH1-2/Vκ4.1. This example illustrates the ability of tolerised HLA-tg to select for antibodies with low immunogenicity from a mixture with other antibodies which induce significant immunogenicity.

The invention claimed is:

1. A method for testing the immunogenicity of a variant antigen in a transgenic mouse model of tolerance in the human immune system, where the variant antigen is derived from a mammalian antigen, and is tested in a transgenic mouse that is transgenic for both human MHC class II molecules and the mammalian antigen, the method comprising:
   (a) obtaining said transgenic mouse that is transgenic for both human MHC class II molecules and the mammalian antigen by backcrossing a human HLA transgenic mouse with mice that are transgenic for the mammalian antigen, wherein the transgenic mouse has tolerance for the mammalian antigen, wherein the tolerance to the mammalian antigen is in the context of human MHC class II, not mouse MHC class II;
   (b) contacting said transgenic mouse with said variant antigen; and
   (c) measuring the immunogenicity of said variant antigen in said transgenic mouse,
   wherein said mouse MHC class II molecule in said transgenic mouse is deleted or rendered inactive, and
   wherein said transgenic mouse is not transgenic for human CD4.

2. A method according to claim 1 wherein said variant antigen is a protein.

3. A method according to claim 2 wherein said variant antigen is a monoclonal antibody.

4. A method according to claim 1 wherein said transgenic mouse is modified to delete or render inactive any mouse genes expressing said antigen or variants of said antigen.

5. A method according to claim 1 wherein said transgenic mouse is modified to delete or render inactive mouse immunoglobulin heavy and light chain genes.

6. A method according to claim 1 wherein said transgenic mouse encodes human immunoglobulin heavy and light chains.

7. A method according to claim 1 wherein said transgenic mouse encodes one or more human proteins.

8. A method according to claim 1 wherein immunogenicity is measured using serum from said transgenic mouse to test for induction of antibodies against said variant antigen.

9. A method according to claim 1 wherein immunogenicity is measured with T cell proliferation or T cell activation assays using mouse blood or tissue samples as a source of mouse T cells.

10. A method according to claim 1 wherein immunogenicity is measured by testing for production of protein-reactive T cells by binding of specific peptide-WIC complexes, testing of T or B cells by measuring cytokine production, proliferation, cell surface marker expression, Ca2+ flux, PCR or DNA fingerprinting or testing for the emergence of specific immune reactive B or T cells.

* * * * *